US011839448B2

(12) United States Patent
Fan et al.

(10) Patent No.: US 11,839,448 B2
(45) Date of Patent: Dec. 12, 2023

(54) INTRAORAL OCT WITH COLOR TEXTURE

(71) Applicant: CARESTREAM DENTAL TECHNOLOGY TOPCO LIMITED, London (GB)

(72) Inventors: Chuanmao Fan, San Jose, CA (US); Victor C. Wong, Pittsford, NY (US); Jean-Marc Inglese, Bussy-Saint-Georges (FR)

(73) Assignee: DENTAL IMAGING TECHNOLOGIES CORPORATION, Quakertown, PA (US)

( * ) Notice: Subject to any disclaimer, the term of this patent is extended or adjusted under 35 U.S.C. 154(b) by 0 days.

(21) Appl. No.: 16/626,984

(22) PCT Filed: Jun. 29, 2017

(86) PCT No.: PCT/US2017/039884
§ 371 (c)(1),
(2) Date: Dec. 27, 2019

(87) PCT Pub. No.: WO2019/005055
PCT Pub. Date: Jan. 3, 2019

(65) Prior Publication Data
US 2020/0129068 A1 Apr. 30, 2020

(51) Int. Cl.
*G01B 9/02091* (2022.01)
*A61B 5/00* (2006.01)
(Continued)

(52) U.S. Cl.
CPC .......... *A61B 5/0066* (2013.01); *A61B 5/0088* (2013.01); *G01B 9/02091* (2013.01);
(Continued)

(58) Field of Classification Search
CPC ... A61B 5/0066; A61B 5/0088; A61B 5/4547; G01B 9/02091; G01B 9/02029; G01B 9/0203; G01J 3/508
See application file for complete search history.

(56) References Cited

U.S. PATENT DOCUMENTS 8,953,911 B1 * 2/2015 Xu ........................ G02B 6/26
385/12
10,107,616 B2 10/2018 Zhou
(Continued)

FOREIGN PATENT DOCUMENTS

CN 101730498 A 6/2010
CN 104870930 A 8/2015

OTHER PUBLICATIONS

International Preliminary Report on Patentability received for PCT Patent Application No. PCT/US2017/039884, dated Jan. 9, 2020, 8 pages.
(Continued)

Primary Examiner — Jonathan M Hansen
(74) Attorney, Agent, or Firm — ALSTON & BIRD LLP

(57) ABSTRACT

An apparatus for acquiring intraoral images of a subject has an OCT imaging apparatus having an OCT light source, a scanner that conveys OCT light toward the subject and returned from the subject, and an interferometer having a reference arm and a sample arm. A reflectance imaging apparatus has a visible light source directed toward the subject and an image sensor that forms a reflectance image from returned light. Processing and control logic are configured to process and combine the returned reflectance image to the OCT measured data. A display shows the combined reflectance image and OCT measured data.

17 Claims, 21 Drawing Sheets

(51) Int. Cl.
    *G02B 6/34*     (2006.01)
    *G06T 11/00*     (2006.01)

(52) U.S. Cl.
    CPC .............. *G02B 6/34* (2013.01); *G06T 11/001* (2013.01); *G06T 2207/10101* (2013.01)

(56) References Cited

U.S. PATENT DOCUMENTS

| | | | |
|---|---|---|---|
| 2008/0062429 A1 | 3/2008 | Liang et al. | |
| 2008/0118886 A1 | 5/2008 | Liang et al. | |
| 2012/0015316 A1* | 1/2012 | Sachdeva | A61C 5/77 433/24 |
| 2014/0213897 A1 | 7/2014 | Iftimia et al. | |
| 2014/0226150 A1* | 8/2014 | Colonna de Lega | G01B 11/2441 356/73 |
| 2016/0148375 A1* | 5/2016 | Oh | A61B 6/032 382/131 |
| 2018/0027159 A1* | 1/2018 | Dillon | A61B 5/0088 348/66 |

OTHER PUBLICATIONS

International Search Report and Written Opinion received for PCT Patent Application No. PCT/US2017/039884, dated Mar. 22, 2018, 10 pages.

Rongguang Liang et al., "Multimodal imaging system for dental caries detection," SPIE Proceedings, Lasers in Dentistry XIII, 6425, 7 pages (Feb. 2007).

Office Action received for Chinese Patent Application No. 201780094204, dated Feb. 1, 2023, 9 pages (English Translation only).

Office Action received for Chinese Patent Application No. 201780094204, dated Feb. 1, 2023, 9 pages.

* cited by examiner

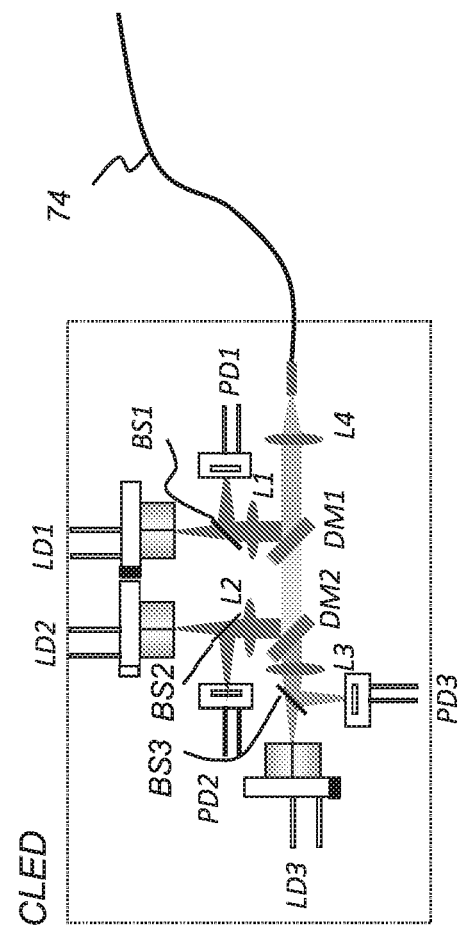

INTRAORAL OCT WITH COLOR TEXTURE

FIELD OF THE INVENTION

The disclosure relates generally to methods and apparatus for optical coherence tomography imaging and more particularly to methods and apparatus for obtaining color reflectance images correlated to OCT content.

BACKGROUND OF THE INVENTION

Optical coherence tomography (OCT) is a non-invasive imaging technique that employs interferometric principles to obtain high resolution, cross-sectional tomographic images that characterize the depth structure of a sample. Particularly suitable for in vivo imaging of human tissue, OCT has shown its usefulness in a range of biomedical research and medical imaging applications, such as in ophthalmology, dermatology, oncology, and other fields, as well as in ear-nose-throat (ENT) and dental imaging.

OCT has been described as a type of "optical ultrasound", imaging reflected energy from within living tissue to obtain cross-sectional data. In an OCT imaging system, light from a wide-bandwidth source, such as a super luminescent diode (SLD) or other light source, is directed along two different optical paths: a reference arm of known length and a sample arm that illuminates the tissue or other subject under study. Reflected and back-scattered light from the reference and sample arms is then recombined in the OCT apparatus and interference effects are used to determine characteristics of the surface and near-surface underlying structure of the sample. Interference data can be acquired by rapidly scanning the sample illumination across the sample. At each of several thousand points, OCT apparatus obtains an interference profile which can be used to reconstruct an A-scan with an axial depth into the material that is a factor of light source coherence. For most tissue imaging applications, OCT uses broadband illumination sources and can provide image content at depths of a few millimeters (mm).

Initial OCT apparatus employed a time-domain (TD-OCT) architecture in which depth scanning is achieved by rapidly changing the length of the reference arm using some type of mechanical mechanism, such as a piezoelectric actuator, for example. TD-OCT methods use point-by-point scanning, requiring that the illumination probe be moved or scanned from one position to the next during the imaging session. More recent OCT apparatus can use a Fourier-domain architecture (FD-OCT) that discriminates reflections from different depths according to the optical frequencies of the signals they generate. FD-OCT methods simplify or eliminate axial scan requirements by collecting information from multiple depths simultaneously and offer improved acquisition rate and signal-to-noise ratio (SNR).

Because of their potential to achieve higher performance at lower cost, FD-OCT systems based on swept-frequency laser sources have attracted significant attention for medical applications that require subsurface imaging in highly scattering tissues. There are two implementations of Fourier-domain OCT: spectral domain OCT (SD-OCT) and swept-source OCT (SS-OCT).

SD-OCT imaging can be accomplished by illuminating the sample with a broadband illumination source and dispersing the reflected and scattered light with a spectrometer onto an array detector, such as a CCD (charge-coupled device) detector, for example. SS-OCT imaging illuminates the sample with a rapid wavelength-tuned laser and collects light reflected during a wavelength sweep using only a single photodetector or balanced photodetector. With both SD-OCT and SS-OCT, a profile of scattered light reflected from different depths is obtained by operating on the recorded interference signals using Fourier transforms, such as Fast-Fourier transforms (FFT), well known to those skilled in the signal analysis arts.

One shortcoming of OCT imaging overall is the absence of corresponding color image content for the scanned surface. Because OCT imaging provides depth data obtained from interferometry effects and signal amplitudes, there is no associated color content available with the OCT reconstruction. For dental surface mapping, the practitioner obtains from the OCT output only the overall shape and contour of intraoral features. There is no available color texture information corresponding to the OCT measured data.

The capability to combine color texture content with OCT reconstruction would help to improve tasks such as tooth visualization, shade matching, segmentation of tooth and supporting structures, lesion detection, and feature recognition. Thus, it can be seen that there would be advantages to an imaging apparatus that provided both OCT depth information and color texture data.

SUMMARY OF THE INVENTION

It is an object of the present disclosure to advance the art of diagnostic imaging and to address the need for providing color texture information that is correlated to OCT scanning data. Certain exemplary method and/or apparatus embodiments herein provide apparatus and methods that combine color texture acquisition with OCT sampling for intraoral imaging applications.

These objects are given only by way of illustrative example, and such objects may be exemplary of one or more embodiments of the invention. Other desirable objectives and advantages inherently achieved by the disclosed methods may occur or become apparent to those skilled in the art. The invention is defined by the appended claims.

According to an aspect of the present disclosure, there is provided an apparatus for acquiring intraoral images comprising an apparatus for acquiring intraoral images of a subject comprising:
  an OCT imaging apparatus comprising an OCT light source, a scanner that conveys OCT light toward the subject and returned from the subject, and an interferometer having a reference arm and a sample arm;
  a reflectance imaging apparatus comprising a visible light source directed toward the subject and an image sensor that forms a reflectance image from returned light;
  processing and control logic configured to process and combine the returned reflectance image to the OCT measured data; and
  a display that shows the combined reflectance image and OCT measured data.

According to an alternate aspect of the present disclosure, there is provided a method for acquiring image data comprising:
  obtaining, for an intraoral surface sample, optical coherence tomography (OCT) data;
  acquiring reflectance image content from the intraoral surface sample;

combining the reflectance image and OCT data content; and rendering the combined reflectance image and OCT data content on a display.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting system optics, for example, are not shown in the drawings in order to simplify description.

FIGS. 6A through 6G show various embodiments of a color light emitter/detector.

DESCRIPTION OF EXEMPLARY EMBODIMENTS

Figure 1:
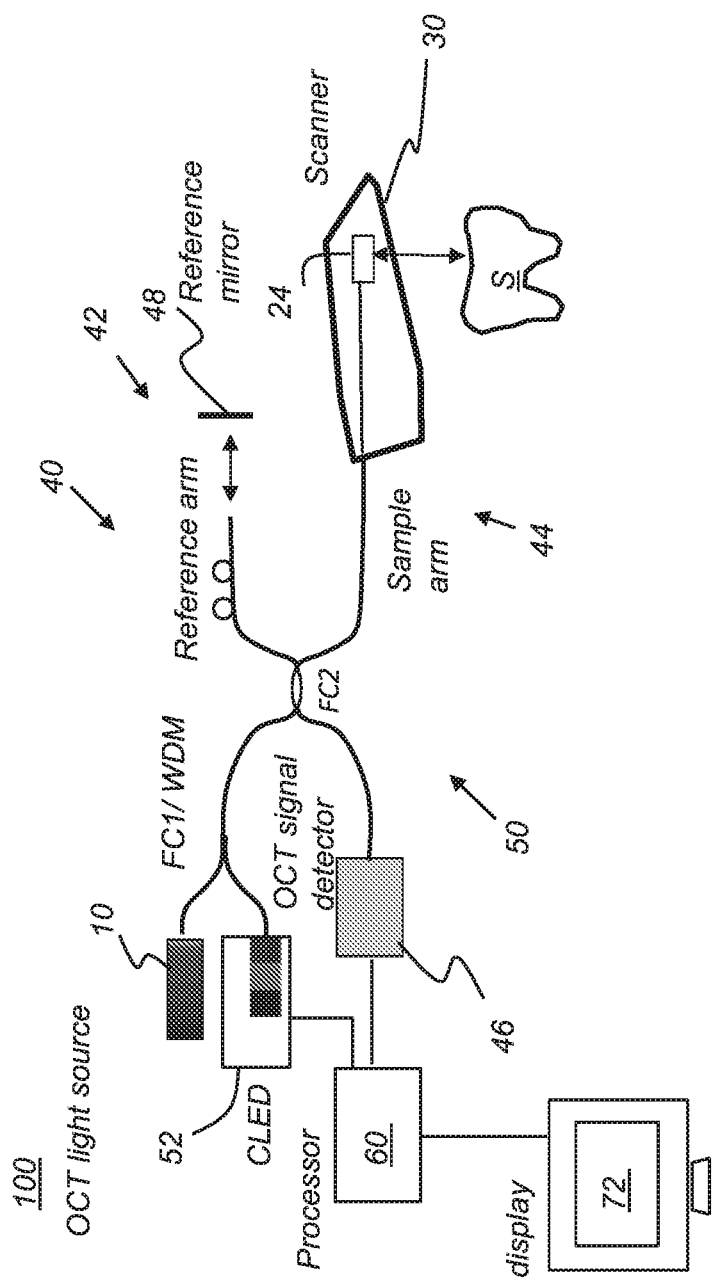
FIG. 1 is a schematic diagram showing an imaging apparatus for combined OCT scanning and color image acquisition.

The following is a description of exemplary method and/or apparatus embodiments of the application, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the term "optics" is used generally to refer to lenses and other refractive, diffractive, and reflective components or apertures used for shaping and orienting a light beam. An individual component of this type is termed an optic.

In the context of the present disclosure, the terms "viewer", "operator", and "user" are considered to be equivalent and refer to the viewing practitioner, technician, or other person who may operate a camera or scanner and may also view and manipulate an image, such as a dental image, on a display monitor. An "operator instruction" or "viewer instruction" is obtained from explicit commands entered by the viewer, such as by clicking a button on the camera or scanner or by using a computer mouse or by touch screen or keyboard entry.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "camera" relates to a device that is enabled to acquire a reflectance, 2-D digital image from reflected visible or NIR light, such as structured light that is reflected from the surface of teeth and supporting structures.

The general term "scanner" relates to an optical system that projects a scanned light beam of broadband near-IR (BNIR) illumination that is directed to the tooth surface through a sample arm and acquired, as scattered light returned in the sample arm, for detecting interference with light from a reference arm used in OCT imaging of a surface. The term "raster scanner" relates to the combination of hardware components that scan light toward a sample, as described in more detail subsequently.

The term "subject" refers to the tooth or other portion of a patient that is being imaged and, in optical terms, can be considered equivalent to the "object" of the corresponding imaging system. This corresponds to the term "sample" that is typically used with reference to OCT imaging.

In the context of the present disclosure, the phrase "broadband light emitter" refers to an illumination or light source that emits a continuous spectrum output over a range of wavelengths at any given point of time. Short-coherence or low-coherence, broadband illumination sources can include, for example, super luminescent diodes, short-pulse lasers, many types of white-light sources, and supercontinuum light sources. Most low coherence length sources of these types have a coherence length on the order of tens of microns or less.

In the context of the present disclosure, the terms "color light", "polychromatic light", and "RGB light" describe visible light illumination that is provided for reflectance imaging. The color image can be considered a reflectance image or color texture image. As is well known in the color imaging arts, a color combiner, such as a dichroic surface that transmits one spectral band and reflects another spectral band, can be used to combine colors for light traveling in one direction and to separate colors for light traveling in the opposite direction. Thus, the general term "combiner" is typically used for a "combiner/separator" device that both combines and separates light according to wavelength and direction along an optical path.

As is well-known to those skilled in the OCT imaging arts, the axial resolution is related to the coherence length of the light source. Thus, the shorter the coherence length, the higher the axial resolution.

Certain exemplary method and/or apparatus embodiments herein can utilize any of the various types of OCT scanning methods, including time-domain or spectral or frequency-domain OCT. Because the speed advantage is of particular interest, the description that follows is primarily directed to embodiments that employ swept-source OCT, a type of frequency-domain OCT that is generally advantageous for faster speed and overall scanning throughput. However, it should be noted that the compressive sampling methods or other available OCT methods can be used to improve the response of time-domain OCT and other types of OCT as well as with SS-OCT. Methods of the present disclosure can also be used where a spectrometer is used for sensing in the OCT system.

According to an embodiment of the present disclosure, there is provided a hybrid imaging apparatus that obtains OCT scanned data with accompanying color texture content for intraoral features.

Referring to the schematic diagram of FIG. 1, there is shown an imaging apparatus 100 for combined OCT scanning and color image acquisition, wherein the color data is inherently registered to the OCT scan data. Imaging apparatus 100 has two light paths for imaging that can combine the OCT and color image content and share the same light guiding components.

In an OCT light path 40, an OCT light source 10 provides illumination for OCT image scanning. Light source 10 can employ a superluminescent diode (SLD) or other source that emits continuous wavelength broadband light. Alternately, light source 10 can be some other type of suitable light source, such as a swept source that emits light with continuously varying spectral content. This light is directed through a first fiber coupler FC1 or wavelength division multiplexer WDM to a second fiber coupler FC2. Fiber coupler FC2 splits the light path into a reference arm 42 and a sample arm 44. Light in reference arm 42 reflects back from a reference mirror 48; this light is coupled back through fiber coupler FC2 and goes to OCT signal detector 46. Light directed to sample arm 44 is directed to the subject or sample S by a scanner 24. Reflected and scattered light from sample S is coupled back through sample arm 44 to fiber coupler FC2 and is conveyed to OCT signal detector 46. The light from reference arm 42 interferes with light from reference arm 44 to provide the OCT scan data for processing and reconstruction.

In a color reflectance imaging path 50, polychromatic or color light is emitted from a color light emitter/detector (CLED) 52 and directed through fiber coupler FC1 or WDM to the second fiber coupler FC2. Coupler FC2 acts as a combiner/separator. The polychromatic visible light is combined with the OCT sample light and is simultaneously directed to sample S through scanner 24, part of an intraoral probe 30. Returned reflected color light from the surface of the tooth or other intraoral feature is conveyed through fiber coupler FC2 back to CLED 52. CLED 52 senses the color content from the reflected light. A control logic processor 60 is in signal communication with OCT signal detector 46, CLED 52 and light source 10 to record and process the OCT output data from interference and combine this data with the color data from the intraoral surface. The resulting combined image content can then be presented on a display 72 and can alternately be transmitted and stored.

Figure 2:
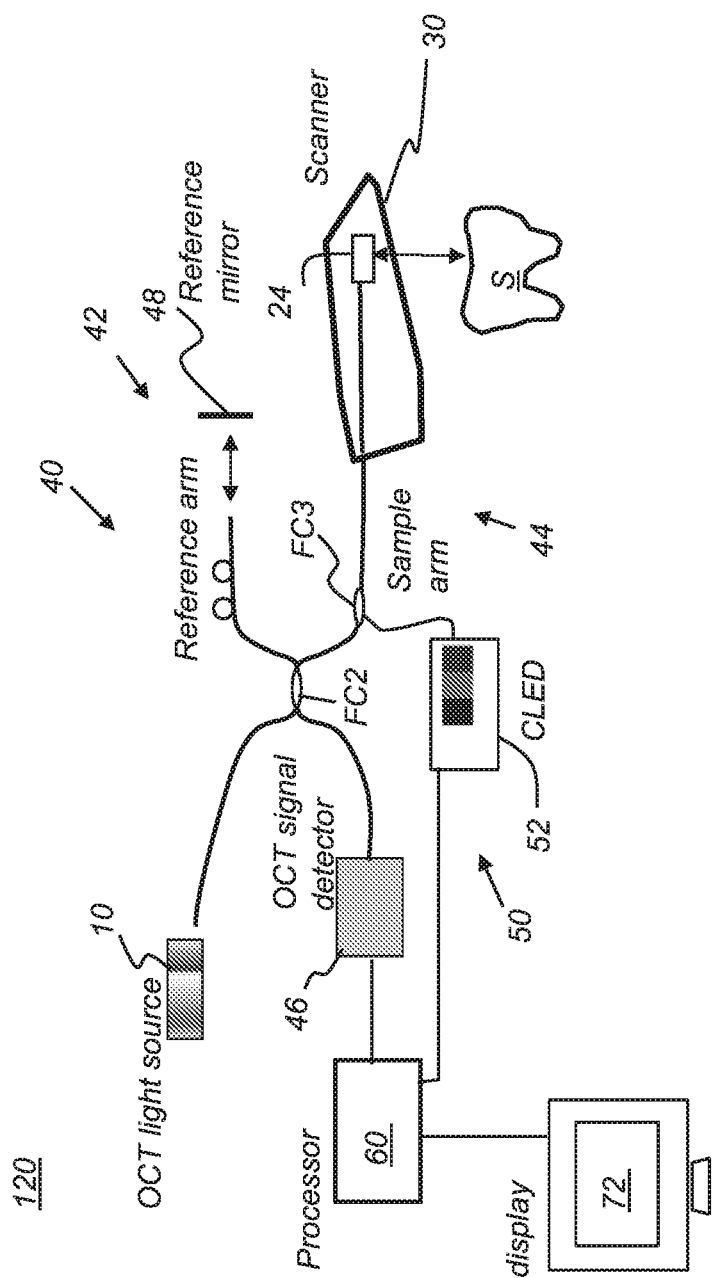
FIG. 2 is a schematic diagram showing an alternate embodiment for an imaging apparatus for combined OCT scanning and color image acquisition.
Figure 3:
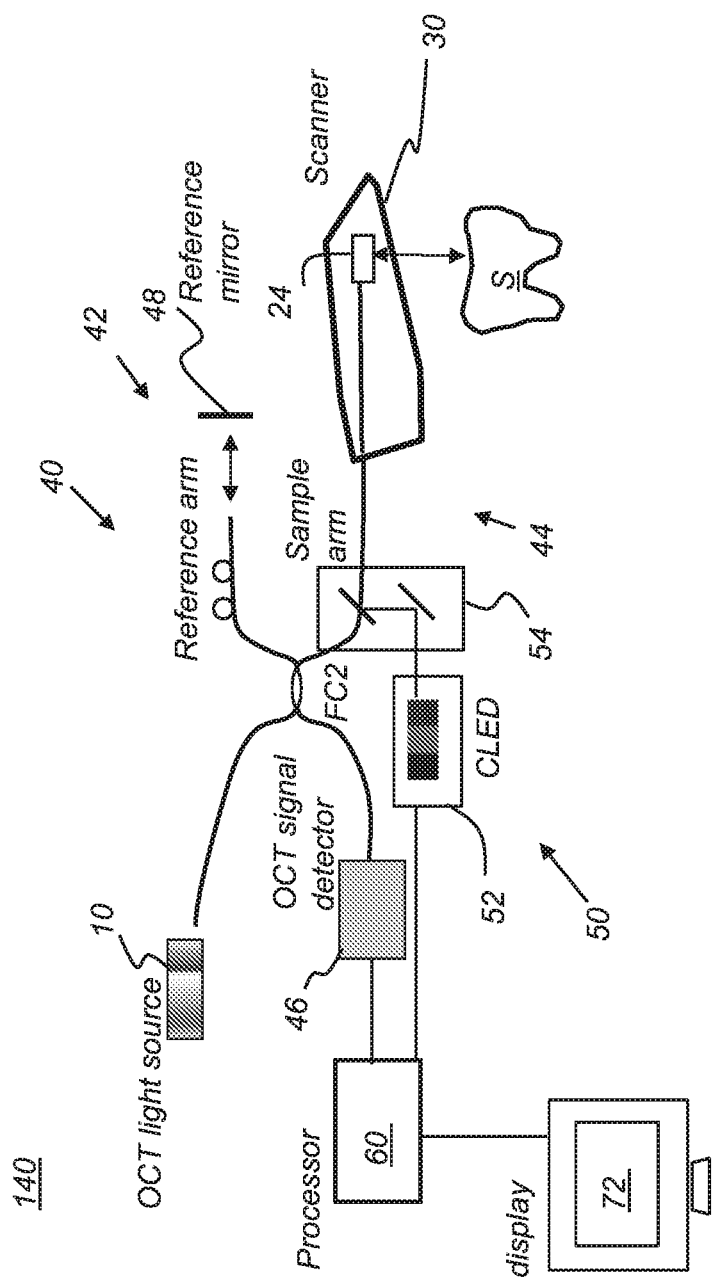
FIG. 3 is a schematic diagram showing another alternate embodiment for an imaging apparatus for combined OCT scanning and color image acquisition.

The schematic diagrams of FIGS. 2 and 3 show similar imaging apparatus 120 and 140 respectively, having slightly different light path arrangements for combining the OCT and reflectance imaging functions. In the FIG. 2 arrangement of imaging apparatus 120, the OCT path is the same as that described previously with respect to imaging apparatus 100 in FIG. 1. The light from color light emitter/detector (CLED) 52 is directed through a fiber coupler FC3 and shares the sample arm with OCT light; this combined light is directed to the subject or sample S through scanner 24. Backscattered color light from the intraoral surface is conveyed through fiber coupler FC3 to color light emitter/detector (CLED) 52 to measure the color content, recorded and processed by processor 60. The resulting combined image content can then be presented on a display 72 and can alternately be transmitted and stored.

In the FIG. 3 configuration of imaging apparatus 140, the OCT path is the same as that described previously with respect to imaging apparatus 100 in FIG. 1. The light from color light emitter/detector (CLED) 52 is directed into the sample path through a dichroic combiner 54, that has a reflective surface and a dichroic surface in the configuration shown. Backscattered color light from the intraoral surface is conveyed back to CLED 52 through combiner 54 for detection and measurement, recorded and processed by processor 60. The resulting combined image content can similarly be presented on a display 72 and can alternately be transmitted and stored.

In each of the FIGS. 1-3 configurations, CLED signal detection and OCT signal detection are synchronized and share the same optical path in the sample arm, to and from the sample probe 30 and its scanner 24. This arrangement provides inherent registration of the polychromatic image content to the OCT data.

Scanning Sequence for OCT Imaging

Figure 4A:
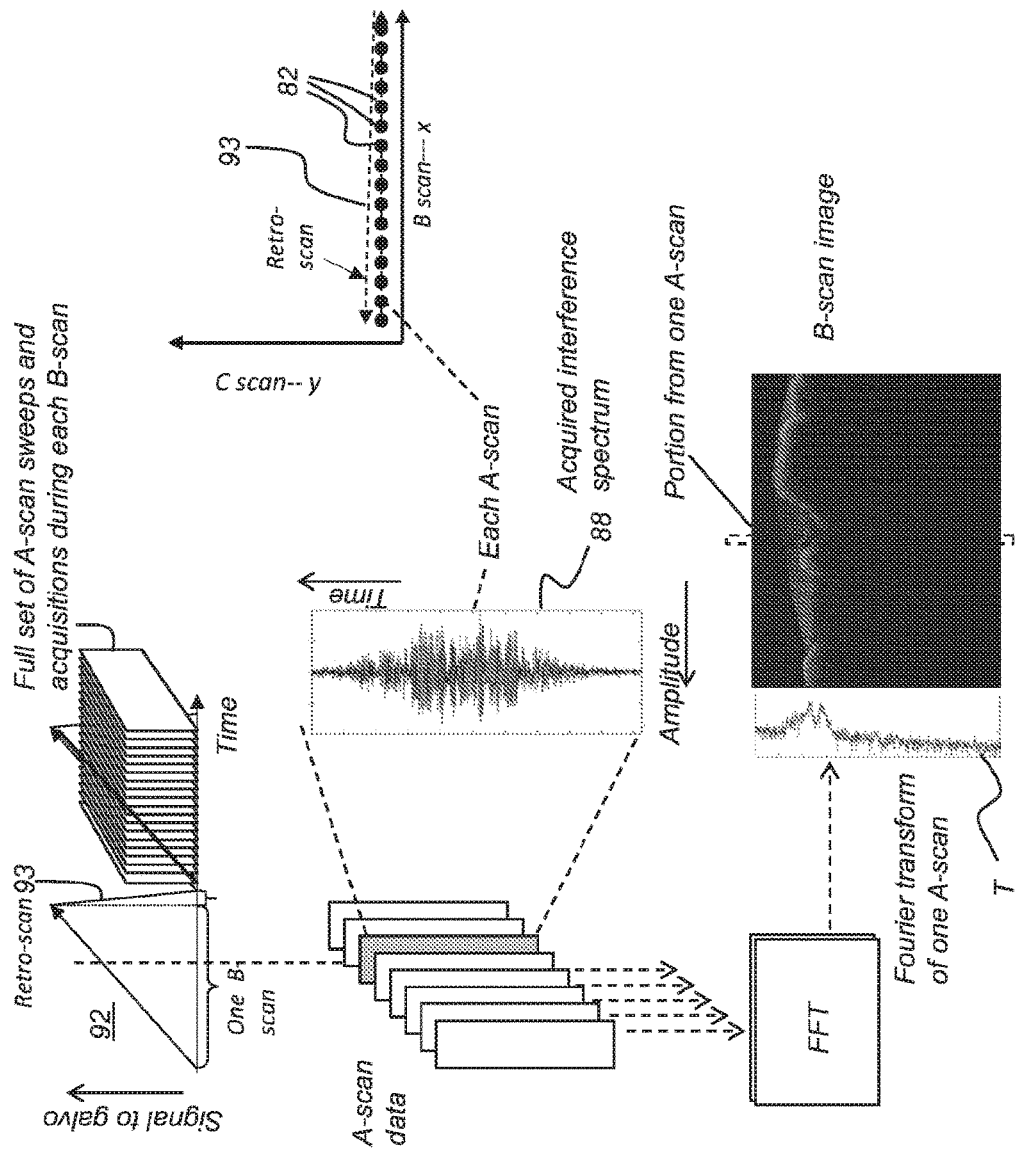
FIGS. 4A and 4B show functional and geometric aspects of OCT imaging.
Figure 4B:
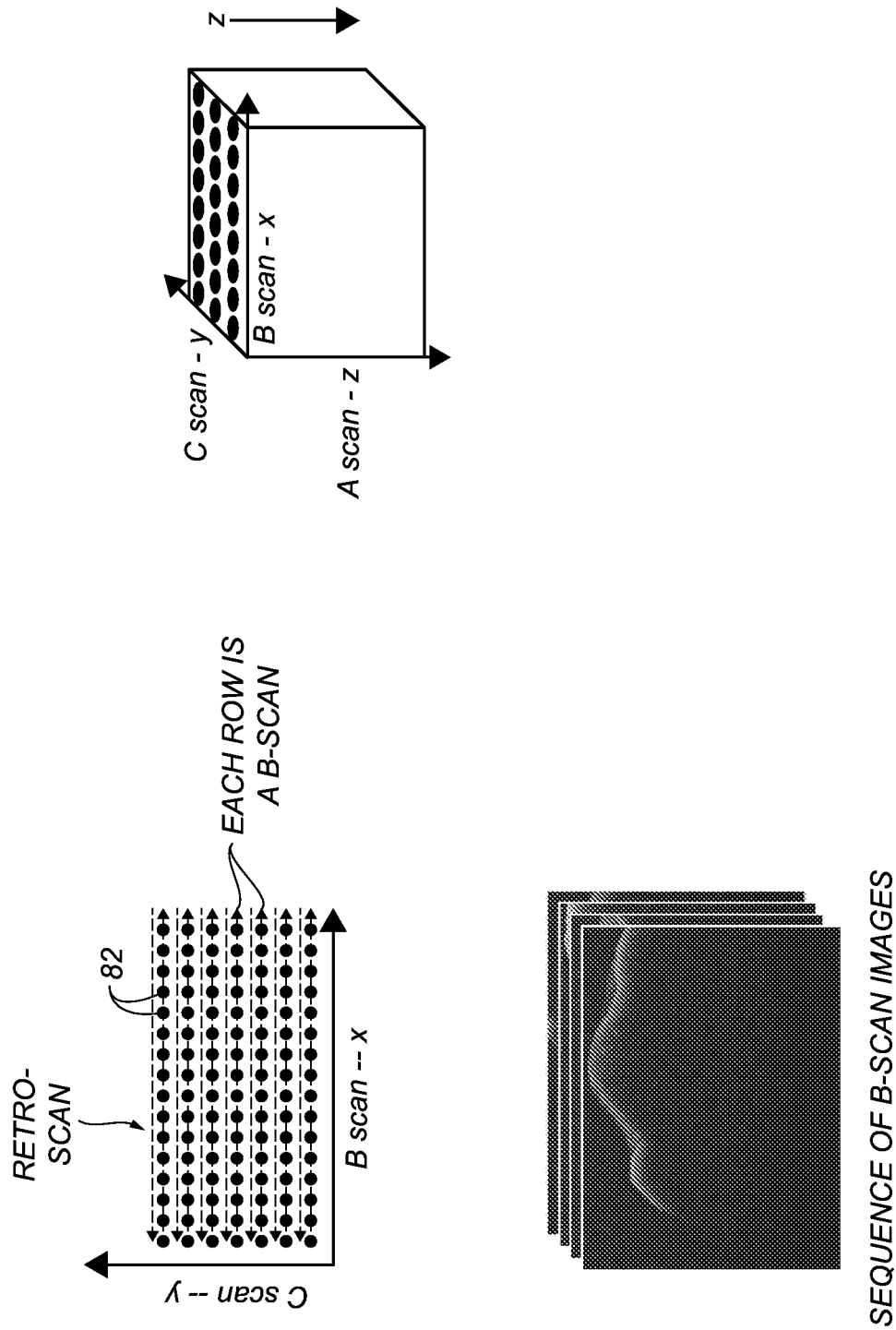

The schematic diagrams of FIGS. 4A and 4B show a scan sequence that can be used for forming tomographic images using the OCT apparatus of the present disclosure in a Fourier domain acquisition. The sequence shown in FIG. 4A shows how a single B-scan image is generated. Raster scanner 24 (FIG. 1) scans the selected light sequence over the subject, sample S, point by point. A periodic drive signal 92 as shown in FIG. 4A is used to drive the raster scanner 24 galvo mirrors to control a lateral scan or B-scan that extends across each row of the sample, shown as discrete points 82 extending in the horizontal direction in FIGS. 4A and 4B. At each of a plurality of points 82 along a line or row of the B-scan, an A-scan or depth scan, acquiring data in the z-axis direction, is generated using successive portions of the selected wavelength band. FIG. 4A shows drive signal 92 for generating a straightforward ascending sequence using raster scanner 24, with corresponding micro-mirror actuations, or other spatial light modulator pixel-by-pixel actuation, through the wavelength band. The retro-scan signal 93, part of drive signal 92, simply restores the scan mirror back to its starting position for the next line; no OCT data is obtained during retro-scan signal 93.

It should be noted that the B-scan drive signal 92 drives the galvo mirror for raster scanner 24 as shown in FIGS. 1-3. At each incremental position, point 82 along the row of the B-scan, an A-scan is obtained. To acquire the A-scan data, the tuned laser or other OCT light source sweeps through a spectral sequence controlled by a programmable filter in the OCT source 10. Thus, in an embodiment in which the light source sweeps through a 30 nm range of wavelengths, this sequence is carried out at each point 82 along the B-scan path. As FIG. 4A shows, the set of A-scan acquisitions executes at each point 82, that is, at each position of the scanner 24. By way of example, there can be 2048 measurements for generating the A-scan at each position 82.

FIG. 4A schematically shows the information acquired during each A-scan. An interference signal 88, shown with DC signal content removed, is acquired over the time interval for each point 82, wherein the signal is a function of the time interval required for the spectral sweep, with the signal that is acquired indicative of the spectral interference fringes generated by combining the light from reference and feedback arms of the OCT interferometer components. The Fourier transform generates a transform T for each A-scan. One transform signal corresponding to an A-scan is shown by way of example in FIG. 4A.

From the above description, it can be appreciated that a significant amount of data is acquired over a single B-scan sequence. In order to process this data efficiently, a Fast-Fourier Transform (FFT) is used, transforming the time-based signal data to corresponding frequency-based data from which image content can more readily be generated.

In Fourier domain OCT, the A scan corresponds to one line of spectrum acquisition which generates a line of depth (z-axis) resolved OCT signal. The B scan data generates a 2-D OCT image along the corresponding scanned line.

Raster scanning is used to obtain multiple B-scan data by incrementing the raster scanner 24 acquisition in the C-scan direction. This is represented schematically in FIG. 4B, which shows how 3-D volume information is generated using the A-, B-, and C-scan data.

As noted previously, the wavelength or frequency sweep sequence that is used at each A-scan point 82 can be modified from the ascending or descending wavelength sequence that is typically used. Arbitrary wavelength sequencing can alternately be used. In the case of arbitrary wavelength selection, which may be useful for some particular implementations of OCT, only a portion of the available wavelengths are provided as a result of each sweep. In arbitrary wavelength sequencing, each wavelength can be randomly selected, in arbitrary sequential order, to be used in the OCT system during a single sweep.

Figure 5:
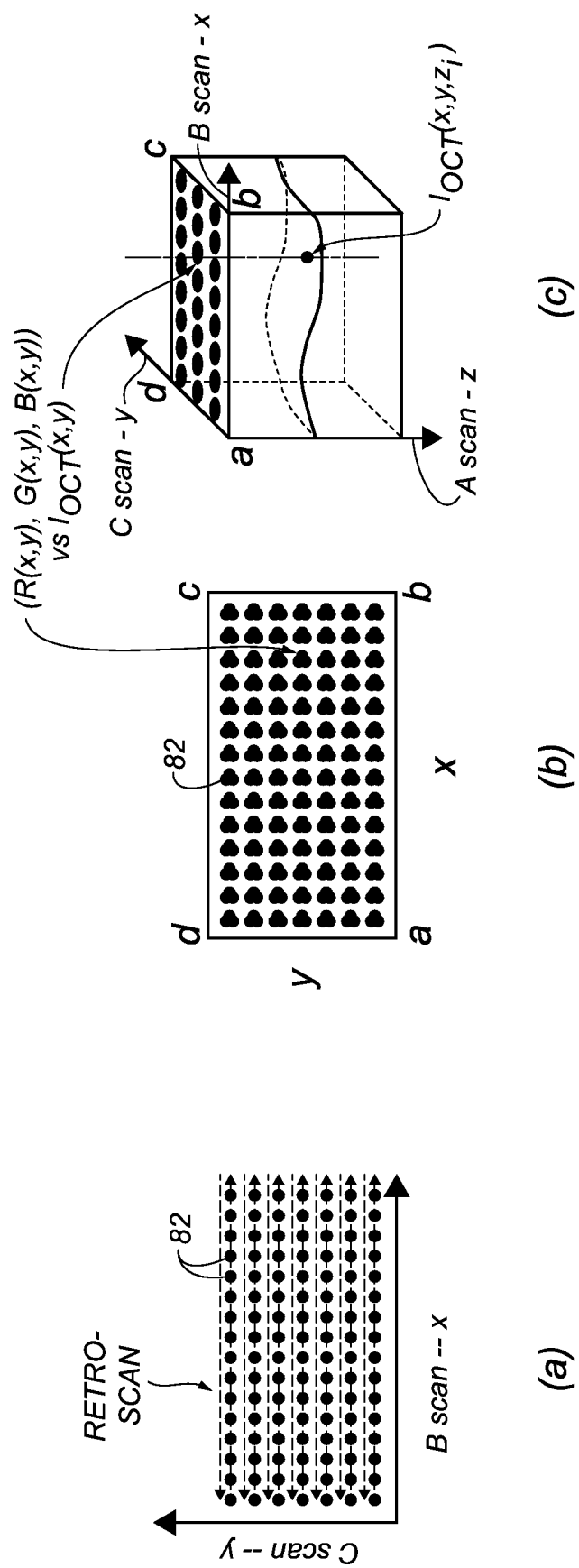
FIG. 5 shows a combined OCT and color scanning scheme in schematic form.

FIG. 5 shows the combined OCT and color scanning scheme in schematic form. Scanner 24 steers both the color light beam and OCT light beam to sample S in a two-dimensional (x, y) raster scan at each point 82, with $x \in [0, L-1]$ indexed along the x scanning axis. The orthogonal component, $x \in [0, M-1]$ is indexed along the y scanning axis. The color signal with three reflectance values (R(x, y), G(x, y), B(x, y)) and the OCT signal $I_{OCT}(x,y)$ with dimension N (for N data points) in the depth direction are acquired corresponding to each scanned position (x, y).

When the 2D scanner 24 scans continuously, a 2D color image is populated with a number L×M of color pixels; correspondingly a 3D OCT volume is reconstructed with values L×M×N. The (R(x, y), G(x, y), B(x, y)) values are inherently registered with $I_{OCT}(x,y)$ along lateral directions. FIG. 5 part (b) shows the inherent mapping provided for the color content at each point 82 corresponding to the OCT scan, with values (R(x, y), G(x, y), B(x, y)) mapped to corresponding $I_{OCT}(x,y)$ measurements. FIG. 5 part (c) shows $I_{OCT}(x,y,z_i)$ with the surface point intensity at $(x,y,z_i)$, wherein $z_i$ is depth of surface from a zero delay line along the A-line OCT signal. The color texture (R(x, y), G(x, y), B(x, y)) is thus mapped directly to the OCT signal at $(x,y,z_i)$.

CLED Structure and Functional Components

Figure 6B:
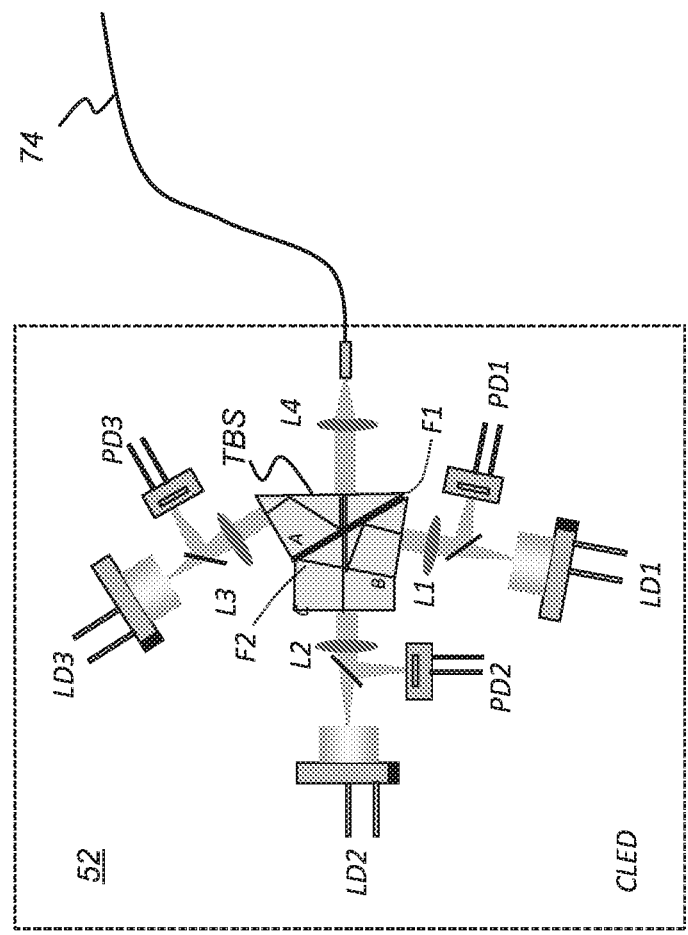
Figure 6C:
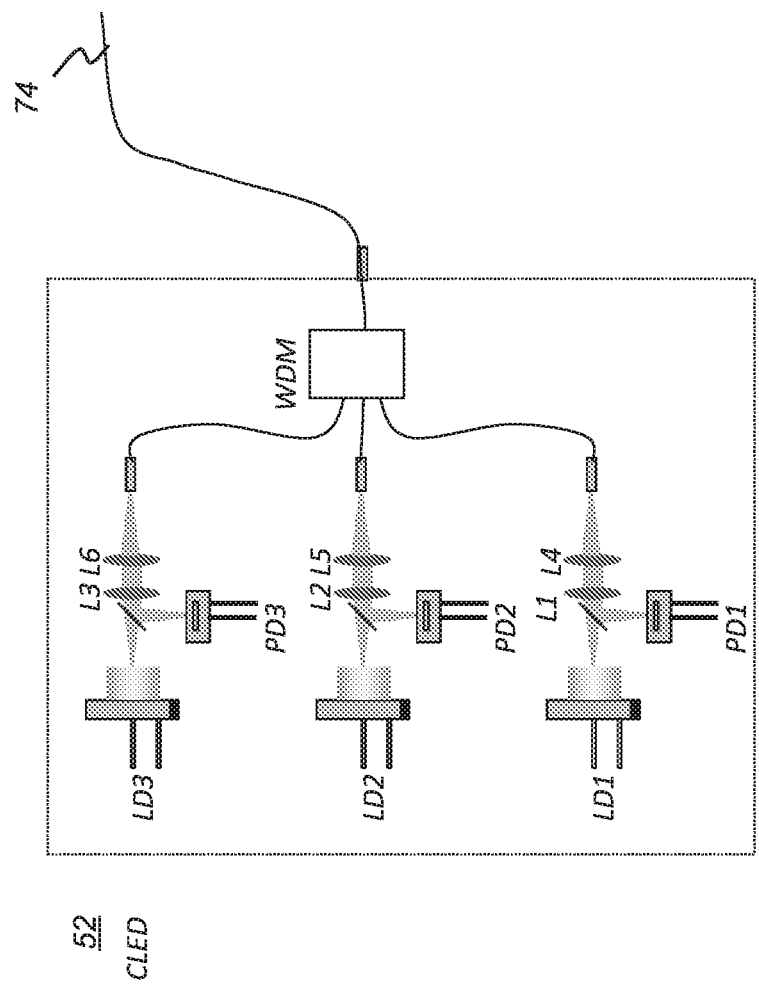

FIGS. 6A, 6B, and 6C show different embodiments of color light emitter/detector CLED 52. Laser diodes LD1, LD2, and LD3 are red, green and blue laser diodes respectively. Lenses L1, L2 and L3 are the corresponding collimation lenses used with each of LD1, LD2, and LD3 to generate collimated light beams.

In the FIG. 6A arrangement, collimated beams are combined onto the same light path by dichroic mirrors DM1 and DM2. DM1 and DM2 have appropriate cutoff wavelengths for corresponding routing of light to and from the light path, such as center wavelengths of red and green laser diodes LD1 and LD2. Lens L4 couples the light from the shared path into a single mode optical fiber 74 to provide full color or polychromatic light. Full color light that has been back-scattered from the sample S is coupled back to CLED 52. Each color light is coupled back to its original channel through beam splitters BS1, BS2, and BS3 and a portion of the light power is directed to corresponding photodiodes PD1, PD2, and PD3 for measurement.

In the FIG. 6B configuration, a trichroic beam splitter TBS with dichroic filters F1 and F2, similar to a Philips prism, combines the light from Red, Green, and Blue laser diodes LD1, LD2, and LD3 onto optical fiber 74, coupled through lens L4. Full color light that has been back-scattered from the subject, sample S, is coupled back to CLED 52. Each color light is coupled back to its original channel through trichroic beam splitter TBS.

In the FIG. 6C configuration, a wave division multiplexer WDM is used for combining and separating the Red, Green, and Blue light from their respective color channels.

Figure 6D:
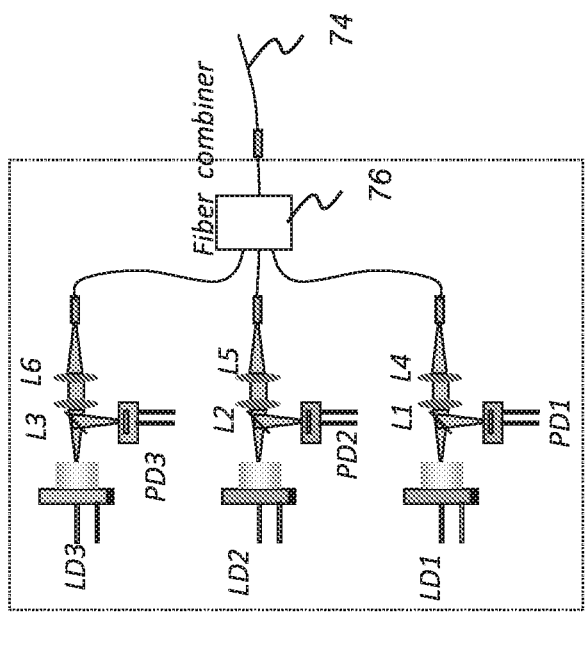

In the FIG. 6D configuration, a fiber combiner 76 is used for combining and separating the Red, Green, and Blue light from their respective color channels.

Figure 6E:
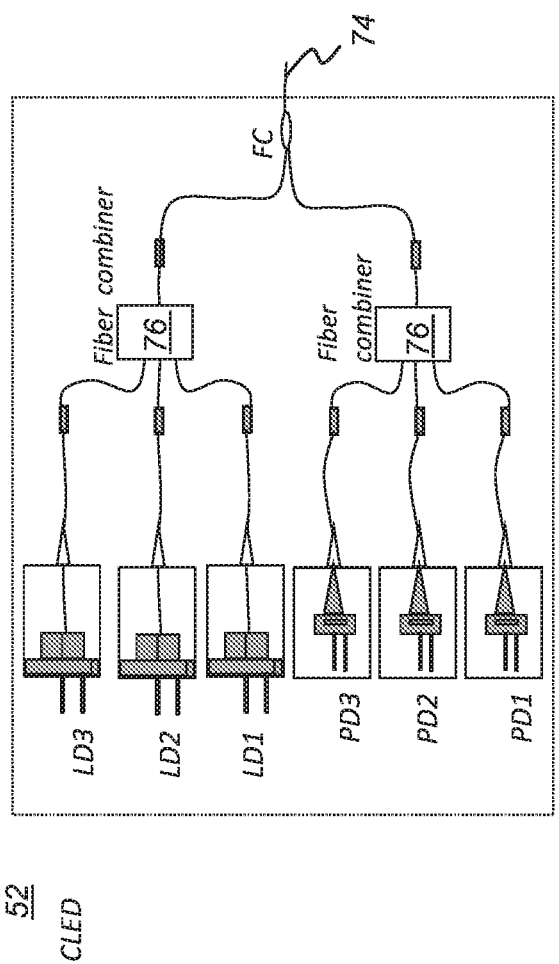

In the FIG. 6E configuration, two fiber combiners 76 are used, one for combining the outgoing Red, Green, and Blue light onto a single channel, the other for separating the returned Red, Green, and Blue light to their respective color channels.

Figure 6F:
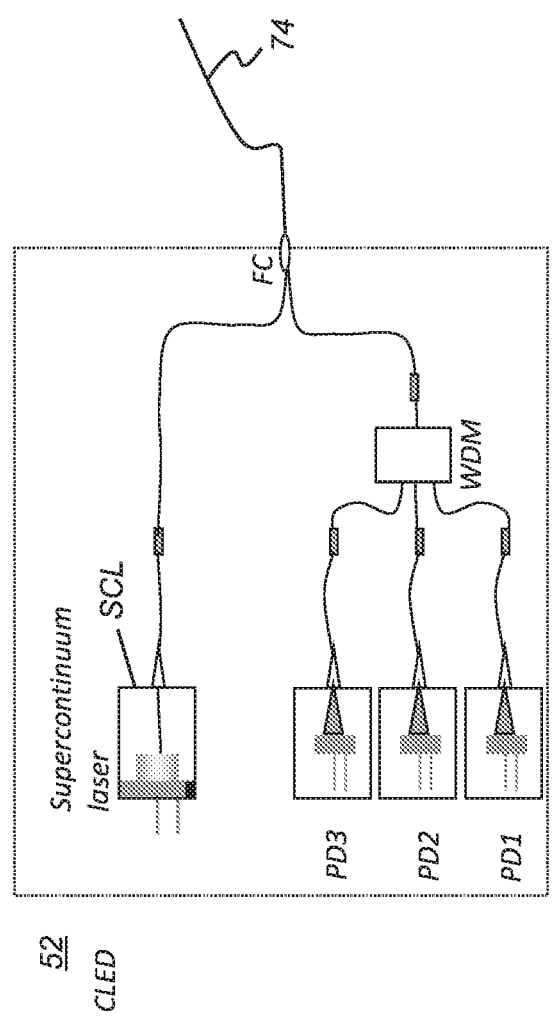

In the FIG. 6F configuration, a wide-bandwidth visible light source, such as a supercontinuum laser SCL, serves as the light source for color imaging. The SCL has a continuous visible spectrum output. Wavelength division multiplexer WDM in the path of returned light separates the backscattered light and redirects the light to each respective photodiode PD1, PD2, PD3. A fiber coupler FC is used to couple the light to and from fiber 74.

Figure 6G:
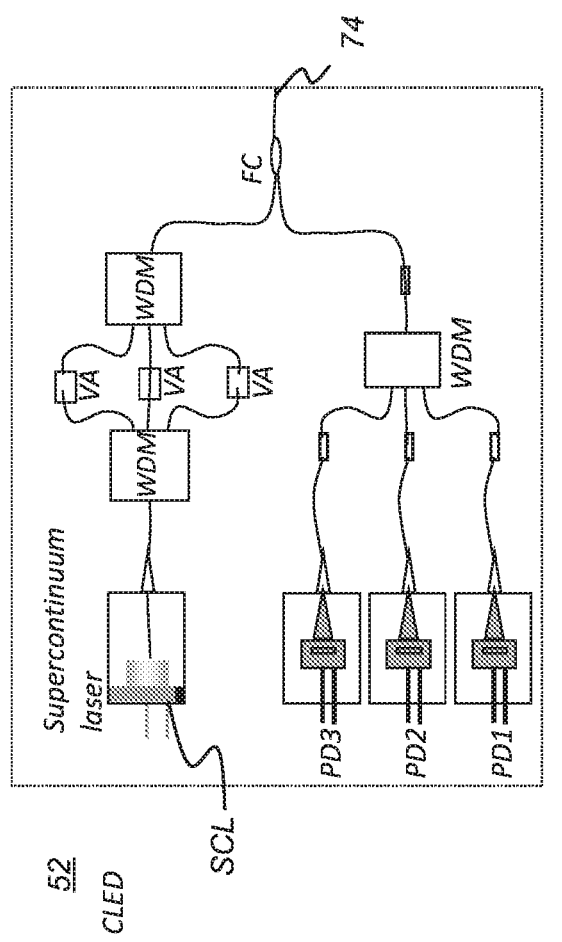

In the FIG. 6G configuration, a pair of wave division multiplexers WDM and variable attenuators VA are used to modulate the SCL light in the emission path. A WDM in the path of returned light separates the backscattered light and redirects the light to each respective photodiode PD1, PD2, PD3. A fiber coupler FC is used to couple the light to and from fiber 74.

Figure 6H:
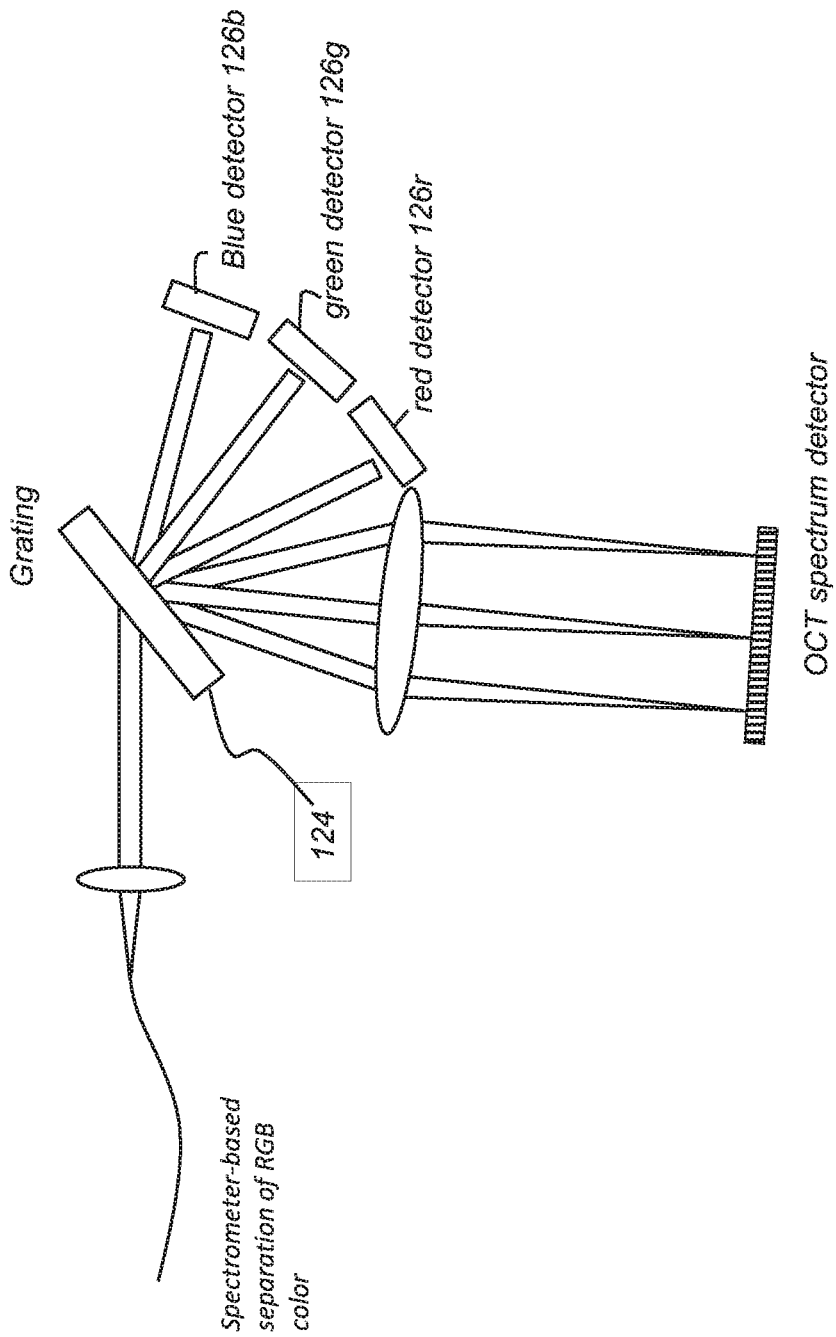
FIG. 6H shows an embodiment in which RGB light detection is performed at the OCT spectrometer.

The FIG. 6H configuration shows an embodiment in which RGB light detection is performed at the OCT spectrometer. Input polychromatic light is coupled to the OCT scanning system, as shown in previous FIGS. 6A-6G. Detection of the polychromatic light utilizes a spectral separator 124, such as a grating or prism to provide spectral separation of the light, directing red, green, and blue light to corresponding detectors 126r, 126g, 126b at appropriate angles, as determined by grating, prism, or other separator characteristics.

Color Image Processing and Calibration

For system calibration and imaging, the reflectance imaging apparatus should be calibrated to a reference standard. R, G, B laser emission is adjusted to provide equal light intensities. Background signals are captured with sample S removed from the sample arm. The R, G, B photodiodes, PD1, PD2, and PD3 respectively, detect background signals that are reflected from the components in the light path. Background signals are subtracted from the R, G, and B signals, respectively. The color image calibration method is similar to that used in color photography which is also adapted in the calculation flow chart of FIG. 7.

Figure 7:
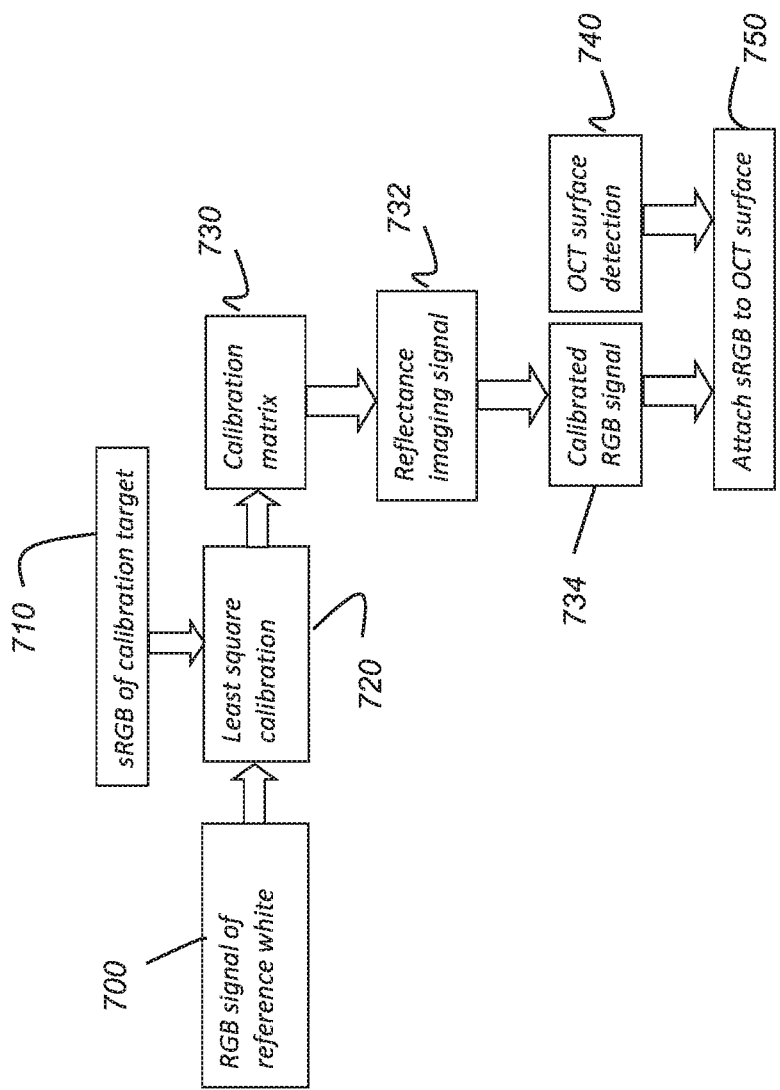
FIG. 7 is a logic flow diagram that shows a sequence for combined color calibration.

FIG. 7 shows a color calibration sequence that can be used for the color scanner that performs both OCT and RGB imaging. RGB signals are obtained from a calibration target, such as a white light reference patch, in a reference imaging step 700. Values from a standard color model, such as sRGB of the reference white patch or other calibration target are acquired in a standard color model step 710. A least squares calculation or other suitable method for obtaining the calibration transform between the RGB signals and sRGB is performed at a calibration step 720, generating a calibration matrix at a transform step 730. The calibration matrix is applied to the RGB signals obtained from a reflectance imaging step 732 to generate a calibrated RGB signal 734. This is combined with OCT surface detection obtained in an OCT surface imaging step 740. An attachment step 750 then combines the OCT surface detection data in register with calibrated RGB data to provide a combined output.

The difference in spectral ranges for the two imaging modes makes the combination of OCT light and RGB color light possible, either using spectral division or amplitude division.

Figure 8:
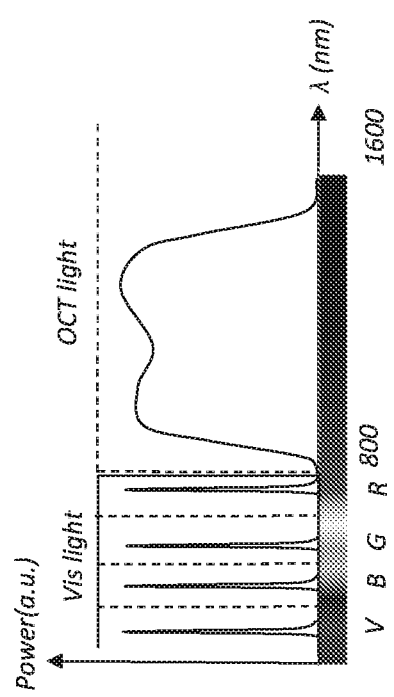
FIG. 8 is a graph that shows spectral ranges for OCT and reflectance imaging.

FIG. 8 shows the spectrum distribution of visible R, G, B light and infrared OCT light waves. As can be readily seen from this mapping, the spectral ranges are non-overlapping. Visible light ranges from about 390 nm to about 700 nm. The infrared light ranges from above 700 nm to about 1600 nm. FIG. 8 also shows related dichroic mirror cut off and bandpass wavelengths for WDM operation. Additional color content can be added to provide more accurate shade matching, such as a violet V wavelength (less than about 450 nm), as shown in the spectral diagram of FIG. 8.

It should be noted that configurations described with reference to FIGS. 1-6H provide inherent registration of the color texture data with OCT data. Because the same optical path in the sample arm is shared, no additional processing is needed in order to register the two different types of data to each other.

Alternate Approach for Combined OCT and Color Texture Imaging

An alternate approach to meeting the need for combined OCT and color texture image data uses an OCT scanner that is coupled with a color preview camera for obtaining the needed image content. When using this alternate approach, processing is needed in order to register the color texture data with the OCT scan content. FIGS. 9A through 9E show different embodiments of an imaging apparatus 200 providing this feature.

Figure 9A:
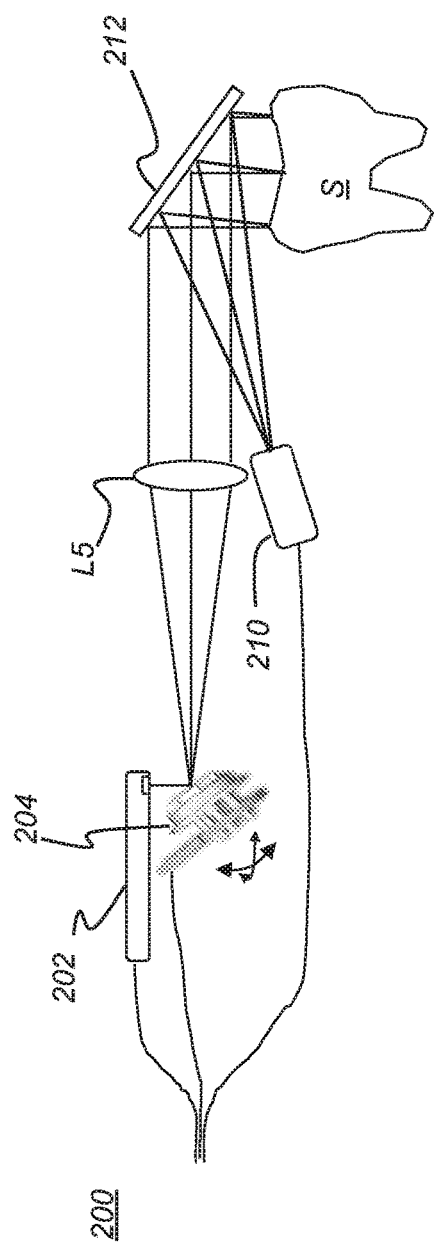
FIGS. 9A-9E show various embodiments of a combined OCT and color image acquisition apparatus using a preview camera.

In the schematic diagram of FIG. 9A, imaging apparatus 200 has a light source 202 that directs collimated light to an OCT scanner 204 for OCT characterization of the subject tooth or other sample S. Lens L5 focuses the light onto the sample S, such as a tooth or other intraoral feature. A mirror 212 folds the optical path to direct light to and from sample S. A camera 210, positionally coupled to the field of view (FOV) of the OCT scanner apparatus, acquires a reflectance (RGB color) image from subject or sample S. White light or RGB light that serves as illumination for reflectance imaging is directed to sample S along the camera imaging path (not shown). Timing synchronization, for example, can be used to associate the reflectance image with the corresponding OCT imaging content for the same portion of the sample S surface. The RGB imaging path must be calibrated to the OCT light path, as described in more detail subsequently.

Figure 9B:
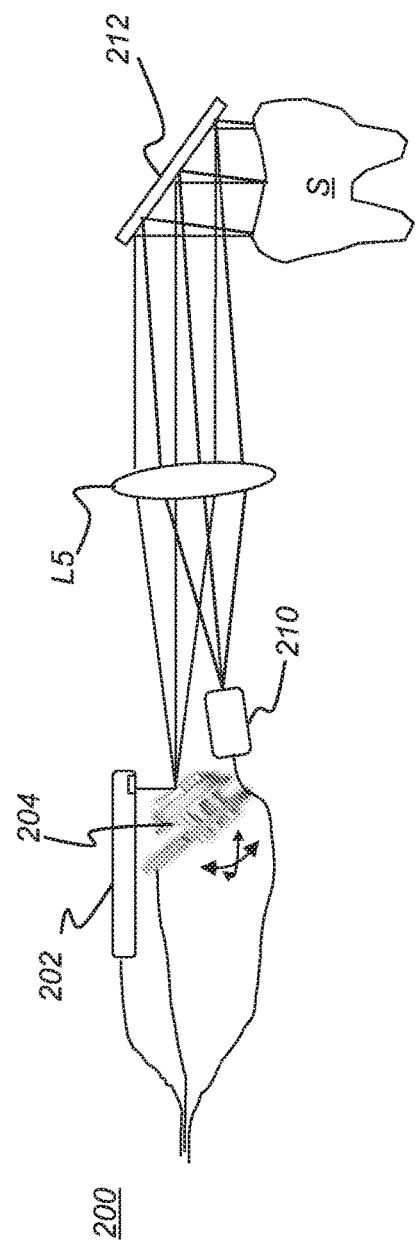

FIG. 9B shows an alternate embodiment of imaging apparatus 200 with a collimated light source 202 and OCT scanner 204 arrangement similar to that of FIG. 9A. Here, lens L5 also forms part of the optical path for camera 210 imaging. Lens L5 focuses the source light for reflectance imaging, as shown.

Figure 9C:
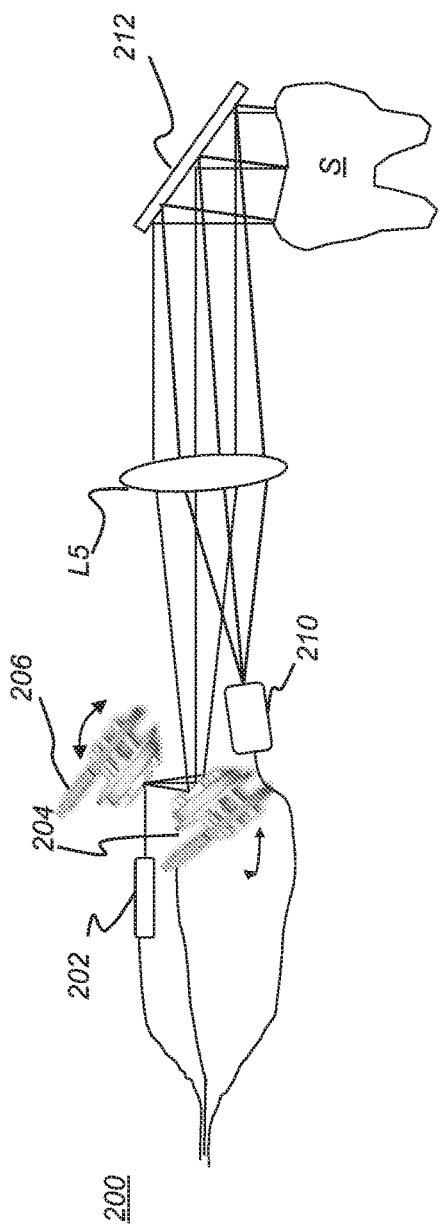

FIG. 9C shows an alternate embodiment of imaging apparatus 200 having a different arrangement of scan mirrors for OCT scanners 204, 206. Here, each OCT scanner is a single-axis scanner. Again, lens L5 also forms part of the optical path for camera 210 imaging.

Figure 9D:
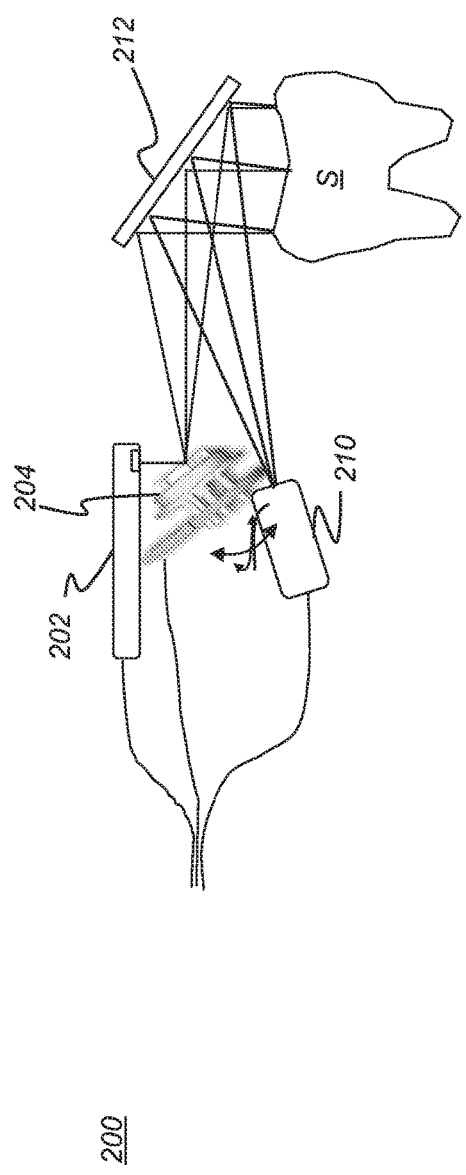

FIG. 9D shows an alternate embodiment of imaging apparatus 200 without lens L5 optics for focus. Here, light source 202 provides a focused OCT beam. RGB illumination goes directly to mirror 212 and is reflected toward the subject, sample S. Returned light from the subject is directed back to camera 210 by mirror 212. Camera 210 contains imaging optics (not shown) for imaging the light reflected back from sample S.

Figure 9E:
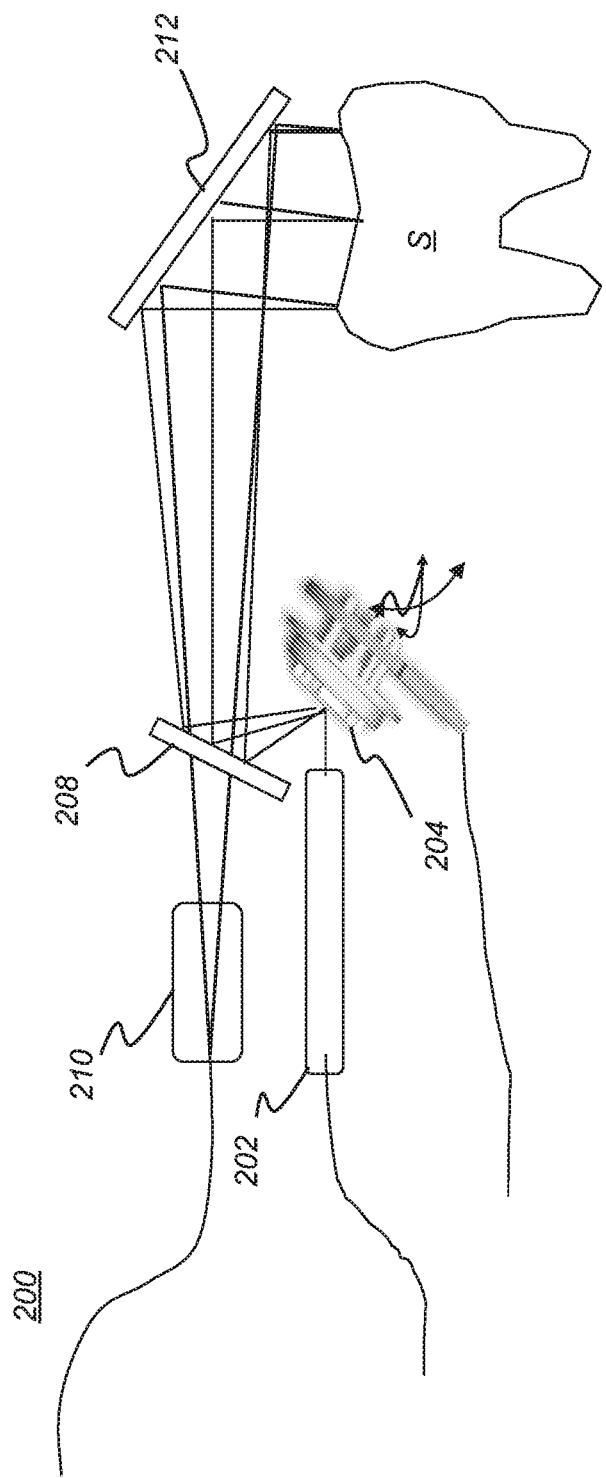

FIG. 9E shows an alternate embodiment of imaging apparatus 200 in which a dichroic surface 208 acts as a "hot mirror", reflecting infrared light from OCT light source 202 and transmitting visible light to and from the reflectance imaging apparatus provided by camera 210.

Registration of Color Texture to OCT Imaging Data

For imaging apparatus that uses OCT scanner coupling with a color preview camera, registration of color texture from the reflectance image to OCT depth characterization data can be performed using various interrelated data acquired in the imaging process.

Additional data for registration can be obtained by projecting the 3D volume generated using OCT in order to generate a 2D grayscale OCT image. Applying a suitable scanner distortion model to correct for OCT distortion can then restore the correct geometry to surface data.

Image projection along the A-line direction mimics 2D pinhole camera imaging in terms of FOV and focus length. This treatment can allow stereo vision calibration methods to be applied to the scanner and preview color camera. Matrix calculation can then be used to translate and rotate the 2D color camera image to a 2D grayscale OCT image. This completes lateral registration. Following this, the 3D surface from OCT imaging can be used for digital impression, with color texture associated with surface locations.

Figure 10A:
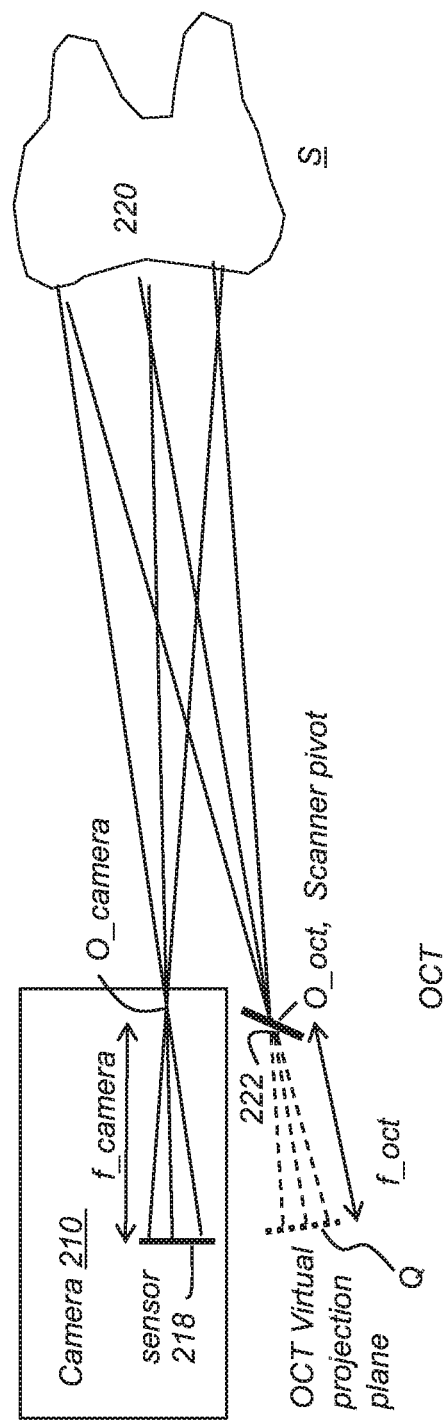
FIGS. 10A and 10B are schematic diagrams that show aspects of registration processing for a tooth as the imaged object using a pinhole camera paradigm.
Figure 10B:
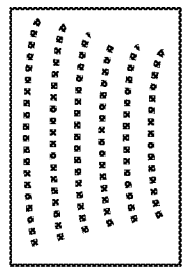
Figure 10B:
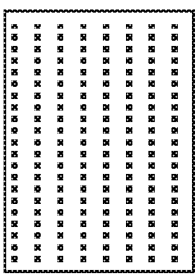

FIGS. 10A and 10B show aspects of registration processing for a tooth 220 as the imaged object using the pinhole camera paradigm. In FIG. 10A, color camera 210 can be modeled as a pinhole camera, with its image sensor at the 2D projection sensor 218 plane. The focus length between the pinhole and sensor 218 plane is labeled f_camera. Labeling O_camera indicates the pinhole origin position for the camera.

Similarly, the three-dimensional OCT volume can back-project onto a virtual projection plane Q along the direction of each A-line, with an OCT scanner pivot 222 regarded as a pinhole source. The focus length f_oct of a virtual OCT camera can be defined such that it generates a projection plane Q of approximately the same size as the color sensor of camera 210. Through OCT scanner calibration, each A-line beam direction can be obtained in a predefined OCT scanner coordinate. For example, a scanner pivot is defined as origin O_oct. The direction of an OCT scan beam can be calibrated with coordinate ($k_x$, $k_y$, $k_z$). Its projection onto a virtual plane is along coordinate $(-k_x, -k_y, -k_z)$. The focus length f_OCT and direction determine the projection position. Due to scanner scanning properties, a fan beam projection shape results, as shown in the OCT projection matrix of FIG. 10B. The pattern shown correctly reflects the actual geometric shape of the scanned object.

After obtaining the OCT projection image and color image, a 3×3 rotation matrix R and a 3×1 translation matrix T can be obtained using well-known stereovision calibration methods. By translation and rotation, two images can thus be registered. However, due to the projection shape difference, a precise matching color for each A-line is not available. Instead, the final color texture for each A-line can be calculated by interpolating the RGB color with surrounding values from the nearest neighbor pixels.

Color texture attachment to the corresponding surface point of the A-line is done similarly to the color texture mapping or correlation method previously described with reference to FIG. 5. The color signal with reflectance values $(R(x, y), G(x, y), B(x, y))$ and the OCT signal $I_{OCT}(x,y)$ with dimension N (for N data points) in the depth direction are acquired corresponding to each scanned position $(x, y)$. These $(R(x, y), G(x, y), B(x, y))$ values can be registered with corresponding $I_{OCT}(x,y)$ data along lateral directions.

Consistent with an embodiment of the present invention, a computer program utilizes stored instructions that perform on image data that is accessed from an electronic memory. As can be appreciated by those skilled in the image processing arts, a computer program for operating the imaging system in an embodiment of the present disclosure can be utilized by a suitable, general-purpose computer system operating as control logic processor 60 as described herein, such as a personal computer or workstation. However, many other types of computer systems can be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present disclosure may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present disclosure may make use of various image manipulation algorithms and processes that are well known. It will be further understood that the computer program product embodiment of the present disclosure may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present disclosure, are not specifically shown or described herein and may be selected from such algorithms, systems, hardware, components and elements known in the art. Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

The invention claimed is:

1. An apparatus for acquiring intraoral images of a subject comprising:
    an OCT imaging apparatus comprising an OCT light source, an interferometer having a reference arm and a sample arm, and a scanner that conveys OCT light toward a plurality of points of the subject and returned from the plurality of points of the subject in the sample arm;
    a reflectance imaging apparatus comprising a visible light source to direct visible light toward a subset of the plurality of points of the subject and an image sensor that forms a reflectance image from returned visible light from the subset of the plurality of points, wherein the visible light and returned visible light are conveyed by the scanner;
    processing and control logic configured to process and combine the returned reflectance image to OCT measured data from the interferometer at least in part by:

generating a projection image based at least in part on OCT measured data from the interferometer;

generating a rotation matrix and a translation matrix for registering the OCT measured data with the reflectance image;

interpolating, for a plurality of pixels of the OCT measured data, a final color texture based at least in part on one or more color values of pixels of the reflectance image registered with neighboring pixels; and a display that shows the combined reflectance image and OCT measured data reflecting the final color texture.

2. The apparatus of claim 1 wherein the processing and control logic is further configured to register the returned reflectance image to the OCT measured data based on operations of the scanner.

3. The apparatus of claim 1 wherein the OCT imaging apparatus is a swept-source OCT imaging apparatus or the OCT light source is a wide-bandwidth light source.

4. The apparatus of claim 1 wherein the scanner determines an optical path to the subject.

5. An apparatus for acquiring intraoral images comprising:

an OCT imaging apparatus comprising an OCT light source, a scanner, and an interferometer having a reference arm and a sample arm, wherein the OCT imaging apparatus is configured to generate a 3D OCT volume having pixel dimensions L×M×N;

a reflectance imaging apparatus comprising a visible light source and a color image sensor, wherein the reflectance imaging apparatus is configured to generate a 2D color image having pixel dimensions L×M;

combining optics that combine the OCT light source and visible light directed toward a 2D arrangement of a plurality of points of an intraoral feature onto the same optical path for projection onto the intraoral feature and that separate the visible light primary components from the OCT light for light returning from the intraoral feature to separately obtain OCT measured data and corresponding color reflectance image data in sequence and correlated for plurality of the 2D arrangement of points of the intraoral feature;

processing and control logic configured to process and combine the returned color reflectance image data and the OCT measured data to overlay the L×M×N OCT volume with the L×M 2D color image to create an overlaid image; and a display that shows the combined color reflectance image and OCT measured data.

6. The apparatus of claim 5 wherein the combining optics provide laser diode visible light.

7. The apparatus of claim 5 wherein the same optical path includes the scanner.

8. The apparatus of claim 5 wherein the combining optics comprise a fiber combiner, a beam splitter, or beam splitter prism.

9. The apparatus of claim 5 wherein the processing and control logic is configured to process and combine the returned color reflectance image data and an OCT surface detected in the OCT measured data.

10. The apparatus of claim 5 wherein the combining optics comprise a wave division multiplexer or a grating.

11. A method for acquiring image data comprising:

obtaining, for an intraoral surface sample, optical coherence tomography (OCT) data having L×M×N pixel dimensions;

acquiring reflectance image content from the intraoral surface sample having L×M pixel dimensions;

combining the reflectance image and OCT data content based at least in part on pixel locations within each of the reflectance image and the OCT data content;

rendering the combined reflectance image and OCT data content in a single image on a display;

registering the reflectance image content to the OCT data by projecting a 3D volume generated from the OCT data to form a 2D grayscale image; and interpolating RGB color with surrounding values from the nearest neighbor pixels.

12. The method of claim 11 further comprising correcting distortion in the 2D grayscale image or applying rotation and translation to the 2D grayscale image or the reflectance image.

13. The method of claim 11 wherein the OCT data is obtained using an OCT imaging apparatus comprising an OCT light source, a scanner, and an interferometer having a reference arm and a sample arm, and wherein the OCT data and the acquired reflectance image content from the intraoral feature are conveyed by the scanner.

14. The method of claim 11 wherein spectral ranges of the OCT and reflectance image content are non-overlapping.

15. The method of claim 11 wherein combining the reflectance image and OCT data content comprises mapping color values of the reflectance image to corresponding points on a surface extracted from the OCT data.

16. The method of claim 11 wherein detection of the acquired reflectance image content is performed at an OCT spectrometer in an OCT signal detector that separates color reflectance image data to the OCT data.

17. The method of claim 11 wherein OCT light for the OCT data and reflectance light for the acquired reflectance image content are separately obtained and correlated for a 2D arrangement of a plurality of points for the intraoral surface sample.

* * * * *